United States Patent
Pop et al.

(10) Patent No.: US 10,993,446 B2
(45) Date of Patent: May 4, 2021

(54) BAKING LIPASE AND METHODS OF USE

(71) Applicant: BASF SE, Ludwigshafen (DE)

(72) Inventors: Cristina Pop, San Diego, CA (US); Adrienne Huston Davenport, San Diego, CA (US); Michael Liszka, San Diego, CA (US); Xuqiu Tan, San Diego, CA (US); Andreas Funke, Illertissen (DE); Jochen Kutscher, Illertissen (DE); Michael Seitter, Illertissen (DE); Stefan Haefner, Ludwigshafen (DE)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 16/079,255

(22) PCT Filed: Feb. 15, 2017

(86) PCT No.: PCT/US2017/017904
§ 371 (c)(1),
(2) Date: Aug. 23, 2018

(87) PCT Pub. No.: WO2017/142904
PCT Pub. Date: Aug. 24, 2017

(65) Prior Publication Data
US 2019/0053501 A1   Feb. 21, 2019

Related U.S. Application Data

(60) Provisional application No. 62/297,582, filed on Feb. 19, 2016.

(51) Int. Cl.
| | |
|---|---|
| *C12N 9/20* | (2006.01) |
| *A21D 8/04* | (2006.01) |
| *C12N 9/04* | (2006.01) |
| *C12N 9/10* | (2006.01) |
| *C12N 9/16* | (2006.01) |
| *C12N 9/26* | (2006.01) |

(52) U.S. Cl.
CPC ........... *A21D 8/042* (2013.01); *C12N 9/0006* (2013.01); *C12N 9/1044* (2013.01); *C12N 9/1074* (2013.01); *C12N 9/16* (2013.01); *C12N 9/2414* (2013.01); *C12Y 101/00* (2013.01); *C12Y 203/02013* (2013.01); *C12Y 204/01019* (2013.01); *C12Y 301/01004* (2013.01); *C12Y 301/01032* (2013.01); *C12Y 301/04003* (2013.01); *C12Y 301/04004* (2013.01); *C12Y 302/01001* (2013.01); *C12Y 302/0106* (2013.01); *C12Y 302/01008* (2013.01); *C12Y 302/01055* (2013.01); *C12Y 302/01133* (2013.01)

(58) Field of Classification Search
None
See application file for complete search history.

(56) References Cited

U.S. PATENT DOCUMENTS

| | | | | |
|---|---|---|---|---|
| 6,110,508 | A * | 8/2000 | Olesen | A21D 8/042 426/20 |
| 6,645,749 | B2 * | 11/2003 | Vind | A21D 8/042 435/195 |
| 8,298,799 | B2 | 10/2012 | Bornscheuer et al. | |
| 2008/0305531 | A1 | 12/2008 | Lam et al. | |
| 2009/0053362 | A1 | 2/2009 | Laan et al. | |

FOREIGN PATENT DOCUMENTS

WO   WO-02/03805 A1   1/2002

OTHER PUBLICATIONS

Watson Team (https://blog.watson-inc.com/baking/author/watson-team) on Oct. 18, 2017, pp. 1-4.*
Altunel et al. (J. Food Sci. Technol., 2017, vol. 54 (6), pp. 1628-1637).*
Aravindan, et al., "Lipase applications in food industry", Indian Journal of Biotechnology, vol. 6, Issue 2, Apr. 2007, pp. 141-158.
Moayedallaie, et al., "Bread improvers: Comparison of a range of lipases with a traditional emulsifier", Food Chemistry, vol. 122, Issue 3, Oct. 2010, pp. 495-499.
Partial Supplementary European Search Report for EP Patent Application No. 17753727.1, dated Jul. 31, 2019, 5 pages.
Schaffarczyk, et al., "Lipases in Wheat Breadmaking: Analysis and Functional Effects of Lipid Reaction Products", Journal of Agricultural and Food Chemistry, vol. 62, Issue 32, 2014, pp. 8229-8237.
International Search Report—PCT/US2017/017904, dated Apr. 4, 2017.
Written Opinion of the International Searching Authority—PCT/US2017/017904, dated May 10, 2017.

* cited by examiner

*Primary Examiner* — Hope A Robinson
(74) *Attorney, Agent, or Firm* — David J. Lorenz

(57) ABSTRACT

Lipase enzymes and methods of using the lipases in a baking for improving the volume, stability, tolerance of a baked product and/or reducing and reducing or eliminating the use of DATEM.

19 Claims, 2 Drawing Sheets
Specification includes a Sequence Listing.

BAKING LIPASE AND METHODS OF USE

CROSS-REFERENCE TO RELATED APPLICATIONS

This application is a continuation of International Application No. PCT/US2017/017904, filed Feb. 15, 2017, which claims the benefit of U.S. Provisional Application No. 62/297,582, filed Feb. 19, 2016.

SEQUENCE LISTING

This application includes an amino acid sequence listing in computer readable form (CRF) in an ASC II text (.txt) file as identified below and is hereby incorporated by reference into the specification of this application in its entirety and for all purposes.

| File Name | Date of Creation | Size (bytes) |
|---|---|---|
| 150300_SequenceListing | Jan. 26, 2016 | 26.3 KB (27,009 bytes) |

TECHNICAL FIELD

Bread has been a staple of human nutrition for thousands of years. Bread is usually made by combining a flour, water, salt, yeast, and/or other food additives to make a dough or paste; then the dough is baked to make bread. Enzymes are known to be useful in baking because of the enzymes effects on the baking process can be similar or better than chemical alternatives. Several different enzymes can be used for making bread, for example lipases have been known to improve the stability and volume of the bread; however, the industry still needs a lipase that improves volume, stability, tolerance, reduces or eliminates the additive diacetyl tartaric acid esters of monoglycerides (DATEM). This disclosure is directed to a lipase that meets or exceeds these industrial requirements.

BRIEF SUMMARY OF THE INVENTION

An embodiment of the invention is: A method for increasing the volume of a baked product comprising: (a) providing a dough; (b) providing a lipase, wherein the lipase is a polypeptide having the amino acid sequence of: SEQ ID NO:1, SEQ ID NO:3, SEQ ID NO:5, SEQ ID NO:7, SEQ ID NO:9, or SEQ ID NO:11; (c) combining the lipase of (b) with the dough of (a) and baking the combination to generate the baked product having an increased volume.

In another embodiment, the dough is a composition comprising: a flour, a salt, water, and yeast.

In another embodiment, the flour is selected from the group consisting of: almond flour, coconut flour, chia flour, corn flour, barley flour, spelt flour, soya flour, hemp flour, potato flour, quinoa, teff flour, rye flour, amaranth flour, arrowroot flour, chick pea (garbanzo) flour, cashew flour, flax meal, macadamia flour, millet flour, sorghum flour, rice flour, tapioca flour, and any combination thereof.

In another embodiment, the yeast is selected from the group consisting of: bakers' yeast, cream yeast, compressed yeast, cake yeast, active dry yeast, instant yeast, osmotolerant yeasts, rapid-rise yeast, deactivated yeast, nutritional yeast, brewer's yeast, distiller's and wine yeast.

In another embodiment, the lipase is a variant polypeptide and the variant polypeptide is at least 80%, 81%, 82%, 83%, 84%, 85%, 86%, 87%, 88%, 89%, 90%, 91%, 92%, 93%, 94%, 95%, 96%, 97%, 98%, or 99% identical to the an amino acid sequence selected from the group consisting of: the polypeptide as set forth in the amino acid sequence of SEQ ID NO:1, SEQ ID NO:3, SEQ ID NO:5, SEQ ID NO:7, SEQ ID NO:9, SEQ ID NO:11, and the variant polypeptide has lipase activity.

In another embodiment, the lipase is a polypeptide encoded by a nucleic acid sequence that encodes that amino acid sequence selected from the group consisting of: a nucleic acid sequence of SEQ ID NO:2, SEQ ID NO:4, SEQ ID NO:6, SEQ ID NO:8, SEQ ID NO:10, SEQ ID NO:12.

In another embodiment, further comprising the addition of a second enzyme. In a further embodiment, the second enzyme comprises a second lipase, an Alpha-amylase; a Glucan 1, 4-alpha-maltotetraohydrolase; an exo-maltotetraohydrolase; a G4-amylase; a Glucan 1,4-alpha-maltohydrolase; a maltogenic alpha-amylase; a cyclodextrin glucanotransferase; a CGTase; a glucoamylase; an Endo-1,4-beta-xylanase; a xylanase; a cellulase; an Oxidoreductases; a Phospholipase A1; a Phospholipase A2; a Phospholipase C; a Phospholipase D; a Galactolipase, triacylglycerol lipase, an arabinofuranosidase, a transglutaminase, a pectinase, a pectate lyase, a protease, or any combination thereof.

In another embodiment, the lipase is active at a range from pH 4.0 to pH 12.0.

In another embodiment, the lipase is active at a temperature range from 20° C. to 60° C.

In another embodiment of the invention, is method for increasing the volume of a baked product without the addition of DATEM comprising: (a) providing a dough; (b) providing a lipase; wherein the lipase is a polypeptide having the amino acid sequence of: SEQ ID NO:1, SEQ ID NO:3, SEQ ID NO:5, SEQ ID NO:7, SEQ ID NO:9, or SEQ ID NO:11, (c) combining the lipase of (b) with the dough of (a) without the addition of DATEM and baking the combination to generate the baked product having an increased volume.

In another embodiment, the dough is a composition comprising: a flour, a salt, water, and yeast.

In another embodiment, the flour is selected from the group consisting of: almond flour, coconut flour, chia flour, corn flour, barley flour, spelt flour, soya flour, hemp flour, potato flour, quinoa, teff flour, rye flour, amaranth flour, arrowroot flour, chick pea (garbanzo) flour, cashew flour, flax meal, macadamia flour, millet flour, sorghum flour, rice flour, tapioca flour, and any combination thereof.

In another embodiment, the yeast is selected from the group consisting of: bakers' yeast, cream yeast, compressed yeast, cake yeast, active dry yeast, instant yeast, osmotolerant yeasts, rapid-rise yeast, deactivated yeast, nutritional yeast, brewer's yeast, distiller's and wine yeast.

In another embodiment, the lipase is a polypeptide having an amino acid sequence selected from the group consisting of: SEQ ID NO:1, SEQ ID NO:3, SEQ ID NO:5, SEQ ID NO:7, SEQ ID NO:9, SEQ ID NO:11.

In another embodiment, the lipase is a variant polypeptide and the variant polypeptide is at least 80%, 81%, 82%, 83%, 84%, 85%, 86%, 87%, 88%, 89%, 90%, 91%, 92%, 93%, 94%, 95%, 96%, 97%, 98%, or 99% identical to the an amino acid sequence selected from the group consisting of: SEQ ID NO:1, SEQ ID NO:3, SEQ ID NO:5, SEQ ID NO:7, SEQ ID NO:9, SEQ ID NO:11, and the variant polypeptide has lipase activity.

In another embodiment, the lipase is a polypeptide encoded by a nucleic acid sequence that encodes that amino acid sequence selected from the group consisting of: SEQ ID NO:1, SEQ ID NO:3, SEQ ID NO:5, SEQ ID NO:7, SEQ ID NO:9, SEQ ID NO:11.

In another embodiment, the method further comprising the addition of a second enzyme. In a further embodiment, the second enzyme comprises a second lipase, an Alpha-amylase; a Glucan 1, 4-alpha-maltotetraohydrolase; an exo-maltotetraohydrolase; a G4-amylase; a Glucan 1,4-alpha-maltohydrolase; a maltogenic alpha-amylase; a cyclodextrin glucanotransferase; a CGTase; a glucoamylase; an Endo-1, 4-beta-xylanase; a xylanase; a cellulase; an Oxi-doreductases; a Phospholipase A1; a Phospholipase A2; a Phospholipase C; a Phospholipase D; a Galactolipase, triacylglycerol lipase, an arabinofuranosidase, a transglutaminase, a pectinase, a pectate lyase, a protease, or any combination thereof.

In another embodiment, the lipase is active at a range from pH 4.0 to pH 12.0.

In another embodiment, the lipase is active at a temperature range from 20° C. to 60° C.

DETAILED DESCRIPTION OF THE INVENTION

Figure 1:
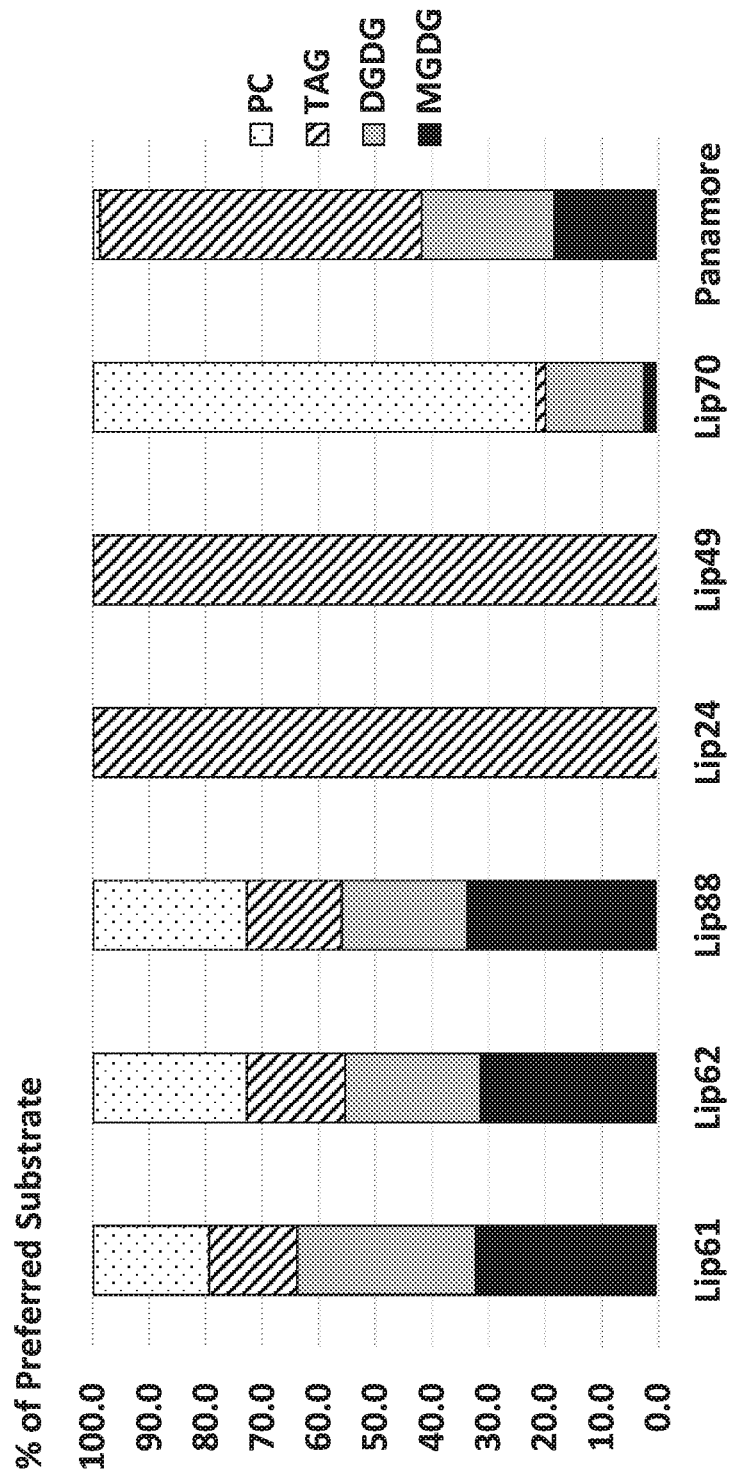
FIG. 1. Lipase specificity for natural substrates in solution.
Figure 2:
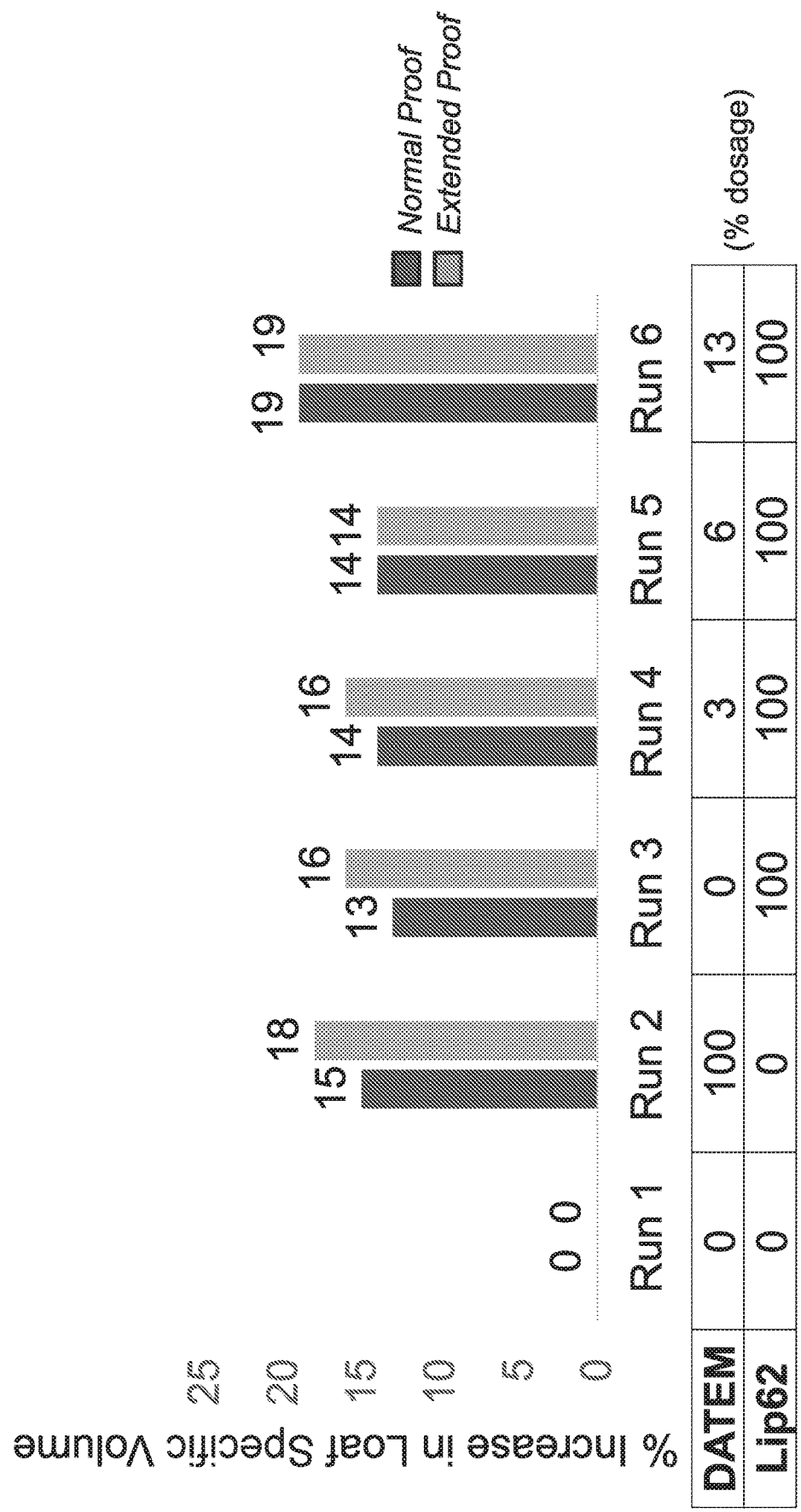
FIG. 2. Lipase and DATEM dosage with Pistolet test

Bread includes, but is not limited to: rolls, buns, pastries, cakes, flatbreads, pizza bread, pita bread, wafers, pie crusts naan, lavish, pitta, focaccia, sourdoughs, noodles, cookies, tortillas, pancakes, crepes, croutons, and biscuits. Baking bread generally involves mixing ingredients to form dough, kneading, rising, shaping, baking, cooling and storage. The ingredients used for making dough generally include flour, water, salt, yeast, and other food additives.

Flour is generally made from wheat and can be milled for different purposes such as making bread, pastries, cakes, biscuits pasta, and noodles. Alternatives to wheat flour include, but are not limited to: almond flour, coconut flour, chia flour, corn flour, barley flour, spelt flour, soya flour, hemp flour, potato flour, quinoa, teff flour, rye flour, amaranth flour, arrowroot flour, chick pea (garbanzo) flour, cashew flour, flax meal, macadamia flour, millet flour, sorghum flour, rice flour, tapioca flour, and any combination thereof. Flour type is known to vary between different regions and different countries around the world.

Yeast breaks down sugars into carbon dioxide and water. A variety of Baker's yeast, which are usually derived from *Saccharomyces cerevisiae*, are known to those skilled in the art including, but not limited to: cream yeast, compressed yeast, cake yeast, active dry yeast, instant yeast, osmotolerant yeasts, rapid-rise yeast, deactivated yeast. Other kinds of yeast include nutritional yeast, brewer's yeast, distiller's and wine yeast.

Sweeteners include but are not limited to: liquid sugar, syrups, white (granulated) sugars, brown (raw) sugars, honey, fructose, dextrose, glucose, high fructose corn syrup, molasses, and artificial sweeteners Emulsifiers include but are not limited to diacetyl tartaric acid esters of monoglycerides (DATEM), sodium stearoyl lactylate (SSL), calcium stearoyl lactylate (CSL), ethoxylated mono- and diglycerides (EMG), polysorbates (PS), and succinylated monoglycerides (SMG).

Other food additives that can be used with the methods of this disclosure include: Lipids, oils, butter, margarine, shortening, butterfat, glycerol, eggs, diary, non-diary alternatives, thickeners, preservatives, colorants, and enzymes.

An enzyme is a biological molecule comprising a sequence of amino acids, wherein the enzyme can catalyze a reaction. Enzyme names are known to those skilled in the art based on the recommendations of the Nomenclature Committee of the International Union of Biochemistry and Molecular Biology (IUBMB). Enzyme names include: an EC (Enzyme Commission) number, recommended name, alternative names (if any), catalytic activity, and other factors. Enzymes are also known as a polypeptide, a protein, a peptide, an amino acid sequence, or is identified by a SEQ ID NO. In this disclosure, the alternative names for enzyme can be used interchangeably.

Different classes of enzymes are known to be useful in baking, including: Alpha-amylase (E.C. 3.2.1.1); Glucan 1, 4-alpha-maltotetraohydrolase (E.C. 3.2.1.60), also known as exo-maltotetraohydrolase, G4-amylase; Glucan 1,4-alpha-maltohydrolase (E.C. 3.2.1.133), also known as maltogenic alpha-amylase; Endo-1,4-beta-xylanase (E.C. 3.2.1.8); Oxi-doreductases; Phospholipase A1 (E.C. 3.1.1.32) Phospholipase A2 (E.C. 3.1.1.4); Phospholipase C (E.C. 3.1.4.3); Phospholipase D (E.C. 3.1.4.4); Galactolipase (E.C. 3.1.1.26), and Protease. Enzymes are used as food ingredients, food additives, and/processing aids.

Lipases (E.C. 3.1.1.3) are hydrolytic enzymes that are known to cleave ester bonds in lipids. Lipases include phospholipases, triacylglycerol lipases, and galactolipases. Lipases have been identified from plants; mammals; and microorganisms including but not limited to: *Pseudomonas, Vibrio, Acinetobacter, Burkholderia, Chromobacterium,* Cutinase from *Fusarium solani* (FSC), *Candida antarctica* A (CalA), *Rhizopus oryzae* (ROL), *Thermomyces lanuginosus* (TLL) *Rhizomucor miehei* (RML), *Aspergillus Niger, Fusarium heterosporum, Fusarium oxysporum, Fusarium culmorum* lipases.

In addition, many lipases, phospholipases, and galactolipases have been disclosed in patents and published patent applications including, but not limited to: WO1993/000924, WO2003/035878, WO2003/089620, WO2005/032496, WO2005/086900, WO2006/031699, WO2008/036863, and WO2011/046812.

Commercial lipases used in food processing and baking including, but not limited to: LIPOPAN™, NOOPAZYME, (available from Novozymes); PANAMORE, CAKEZYME, and BAKEZYME (available from DSM); and GRIND-AMYL EXEL 16, GRINDAMYL POWERBAKE, and TS-E 861 (available from Dupont/Danisco).

A lipase of this disclosure is an isolated, synthetic, or recombinant polypeptide as set forth in the amino acid sequence of SEQ ID NO:1, SEQ ID NO:3, SEQ ID NO:5, SEQ ID NO:7, SEQ ID NO:9, SEQ ID NO:11.

A lipase of the disclosure is an isolated, synthetic, or recombinant polypeptide encoded by a polynucleotide as set forth in the nucleic acid sequence of SEQ ID NO:2, SEQ ID NO:4, SEQ ID NO:6, SEQ ID NO:8, SEQ ID NO:10, SEQ ID NO:12.

The lipase having an amino acid sequence of SEQ ID NO:1 is encoded by the polynucleotide having a nucleic acid sequence of SEQ ID NO:2, or a polynucleotide variant of SEQ ID NO:2 that encodes the amino acid sequence of SEQ ID NO:1. The lipase having an amino acid sequence of SEQ ID NO:3 is encoded by the polynucleotide having a nucleic acid sequence of SEQ ID NO:4, or a variant of SEQ ID NO:4 that encodes the amino acid sequence of SEQ ID NO:3. The lipase having an amino acid sequence of SEQ ID NO:5 is encoded by the polynucleotide having a nucleic acid sequence of SEQ ID NO:6, or a variant of SEQ ID NO:6 that encodes the amino acid sequence of SEQ ID NO:5. The lipase having an amino acid sequence of SEQ ID NO:7 is encoded by the polynucleotide having a nucleic acid sequence of SEQ ID NO:8, or a variant of SEQ ID NO:8 that encodes the amino acid sequence of SEQ ID NO:7. The lipase having an amino acid sequence of SEQ ID NO:9 is encoded by the polynucleotide having a nucleic acid sequence of SEQ ID NO:10, or a variant of SEQ ID NO:10 that encodes the amino acid sequence of SEQ ID NO:9. The lipase having an amino acid sequence of SEQ ID NO:11 is encoded by the polynucleotide having a nucleic acid sequence of SEQ ID NO:12, or a variant of SEQ ID NO:12 that encodes the amino acid sequence of SEQ ID NO:11.

A lipase of this disclosure is an isolated, synthetic, or recombinant variant polypeptide comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to the full length enzymatically active polypeptide of the amino acid sequence comprising or selected from the group consisting of: SEQ ID NO:1, SEQ ID NO:3, SEQ ID NO:5, SEQ ID NO:7, SEQ ID NO:9, and SEQ ID NO:11, and wherein the variant polypeptide has lipase activity.

A lipase of this disclosure, is an isolated, synthetic, or recombinant variant polypeptide comprising an enzymatically active polypeptide of the amino acid sequence comprising or selected from the group consisting of: SEQ ID NO:1, SEQ ID NO:3, SEQ ID NO:5, SEQ ID NO:7, SEQ ID NO:9, and SEQ ID NO:11 and an amino acid substitution, an amino acid insertion, an amino acid deletion, or any combination thereof, wherein the variant polypeptide has lipase activity.

In a further embodiment, the variant polypeptide having an amino acid substitution can be a conservative amino acid substitution. A "conservative amino acid substitution" means replacement of one amino acid residue in an amino acid sequence with a different amino acid residue having a similar property at the same position compared to the parent amino acid sequence. Some examples of a conservative amino acid substitution include but are not limited to replacing a positively charged amino acid residue with a different positively charged amino acid residue; replacing a polar amino acid residue with a different polar amino acid residue; replacing a non-polar amino acid residue with a different non-polar amino acid residue, replacing a basic amino acid residue with a different basic amino acid residue, or replacing an aromatic amino acid residue with a different aromatic amino acid residue.

In a further embodiment, the variant polypeptide having an amino acid substitution can be a replacement of one amino acid residue for any other amino acid residue, wherein the variant polypeptide has lipase activity.

In a further embodiment, the variant polypeptide having lipase activity is a "mature polypeptide." A mature polypeptide means an enzyme in its final form including any post-translational modifications, glycosylation, phosphorylation, truncation, N-terminal modifications, C-terminal modifications, signal sequence deletion. A mature polypeptide can vary depending upon the expression system, vector, promoter, and/or production process.

In a further embodiment, a lipase is active over a broad pH at any single point within the range from about pH 4.0 to about pH 12.0. In an embodiment, the lipase is active over a range of pH 4.0 to pH 11.0, pH 4.0 to pH 10.0, pH 4.0 to pH 9.0, pH 4.0 to pH 8.0, pH 4.0 to pH 7.0, pH 4.0 to pH 6.0, or pH 4.0 to pH 5.0. In another embodiment the lipase is active at pH 4.0, pH 4.5, pH 5.0, pH 5.5, pH 6.0, pH 6.5, pH 7.0, pH 7.5, pH 8.0, pH 8.5, pH 9.0, pH 9.5, pH 10.0, pH 10.5, pH 11.0, pH 11.5, pH 12.0, and pH 12.5.

In a further embodiment, a lipase is active over a broad temperature used in at any time during a baking process, wherein the temperature is any point in the range from about 20° C. to about 60° C. In another embodiment, the lipase is active at a temperature range from 20° C. to 55° C., 20° C. to 50° C., 20° C. to 45° C., 20° C. to 40° C., 20° C. to 35° C., 20° C. to 30° C., or 20° C. to 25° C. In another embodiment the lipase is active at a temperature of at least 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., or higher temperatures.

"Sequence Identity" means a comparison of a first amino acid sequence to a second amino acid sequence, or a comparison of a first nucleic acid sequence to a second nucleic acid sequence and is calculated as a percentage based on the comparison.

Generally, the created alignment can be used to calculate the sequence identity by one of two different approaches. In the first approach, both, mismatches at a single position and gaps at a single position are counted as non-identical positions in final sequence identity calculation. In the second approach, mismatches at a single position are counted as non-identical positions in final sequence identity calculation; however, gaps at a single position are not counted (ignored) as non-identical positions in final sequence identity calculation. In other words, in the second approach gaps are ignored in final sequence identity calculation. The differences between these two approaches, counting gaps as non-identical positions vs ignoring gaps, at a single position can lead to variability in sequence identity value between two sequences.

In an embodiment of this disclosure, sequence identity is determined by a program, which produces an alignment, and calculates identity counting both mismatches at a single position and gaps at a single position as non-identical positions in final sequence identity calculation. For example program Needle (EMBOS), which has implemented the algorithm of Needleman and Wunsch (Needleman and Wunsch, 1970, J. Mol. Biol. 48: 443-453), and which calculates sequence identity by first producing an alignment between a first sequence and a second sequence, then counting the number of identical positions over the length of the alignment, then dividing the number of identical residues by the length of an alignment, then multiplying this number by 100 to generate the % sequence identity [% sequence identity=(# of Identical residues/length of alignment)×100)].

In another embodiment of this disclosure, sequence identity can be calculated from a pairwise alignment showing both sequences over the full length, so showing the first sequence and the second sequence in their full length ("Global sequence identity"). For example program Needle (EMBOSS) produces such alignments; % sequence identity=(# of Identical residues/length of alignment)×100)].

In another embodiment of this disclosure, sequence identity can be calculated from a pairwise alignment showing only a local region of the first sequence or the second sequence ("Local Identity"). For example program Blast (NCBI) produces such alignments; % sequence identity=(# of Identical residues/length of alignment)×100)].

In an embodiment of the disclosure, the lipase can be used in combination with at least one other enzyme or a second enzyme. In another embodiment, the second enzyme comprises or is selected from the group consisting of: an Alpha-amylase; a Glucan 1, 4-alpha-maltotetraohydrolase, also known as exo-maltotetraohydrolase, G4-amylase; a Glucan 1,4-alpha-maltohydrolase, also known as maltogenic alpha-amylase, a cyclodextrin glucanotransferase, a glucoamylase; an Endo-1,4-beta-xylanase; a xylanase, a cellulase, an Oxidoreductases; a Phospholipase A1; a Phospholipase A2; a Phospholipase C; a Phospholipase D; a Galactolipase, triacylglycerol lipase, an arabinofuranosidase, a transglutaminase, a pectinase, a pectate lyase, a a protease, or any combination thereof. In another embodiment, the enzyme combination is the lipase disclosed herein and a maltogenic alpha-amylase, or the enzyme combination is the lipase disclosed herein, a maltogenic alpha-amylase, and a xylanase.

In another embodiment of the disclosure, the lipase can be a hybrid of more than one lipase enzymes. A "hybrid" or "chimeric" or "fusion protein" means that a domain of a first lipase of the disclosure is combined with a domain of a second lipase to form a hybrid lipase and the hybrid has lipase activity. In one embodiment a domain of a lipase of this disclosure is combined with a domain of a commercially available lipase, such as LIPOPAN (available from Novozymes), or PANAMORE (available from DSM) to form a hybrid lipase and the hybrid has lipase activity.

Industrial enzymes are usually recombinant proteins produced using bacteria, fungi, or yeast expression systems. "Expression system" also means a host microorganism, expression hosts, host cell, production organism, or production strain and each of these terms can be used interchangeably for this disclosure. Examples of expression systems include but are not limited to: *Aspergillus niger, Aspergillus oryzae, Hansenula polymorpha, Thermomyces lanuginosus, Fusarium oxysporum, Fusarium heterosporum, Escherichia coli, Bacillus*, preferably *Bacillus subtilis*, or *Bacillus licheniformis, Pseudomonas*, preferably *Pseudomonas fluorescens, Pichia pastoris* (also known as *Komagataella phaffii*), *Myceliopthora thermophile* (C1), *Schizosaccharomyces pombe, Trichoderma*, preferably *Trichoderma reesei*. In an embodiment the lipase of this disclosure is produced using the expression system listed above.

Lipases are known to be useful for other industrial applications. In an embodiment of this disclosure, the lipase is used in a detergent. In an embodiment of this disclosure, the lipase is used in personal care products such as contact lens solution. In another embodiment, the lipase of this disclosure is used in the processing of textiles such as leather manufacturing. In another embodiment, the lipase of this disclosure can be used in pulp and paper processing. In a further embodiment, the pulp and paper processing is pitch control, or deinking. In another embodiment, a lipase of this disclosure can be used for manufacturing biodiesel. In another embodiment, a lipase of this disclosure can be used for cheese ripening. In another embodiment, lipases of this disclosure can be used in preparing a meat flavor and/or aroma. In another embodiment, a lipase of this disclosure can be used in the modification of oils & fats. In another embodiment, a lipase of this disclosure can be used in enzymatic oil degumming. In another embodiment, a lipase of this disclosure can be used in the production of ethanol.

The term "baked products" as used herein includes baked products such as bread, crispy rolls, sandwich bread, buns, baguette, ciabatta, croissants, as well as fine bakery wares like donuts, brioche, stollen, cakes, muffins, etc.

The term "dough" as used herein is defined as a mixture of flour, salt, yeast and water, which can be kneaded, molded, shaped or rolled prior to baking. In addition also other ingredients such as sugar, margarine, egg, milk, etc. might be used. The term includes doughs used for the preparation of baked goods, such as bread, rolls, sandwich bread, baguette, ciabatta, croissants, sweet yeast doughs, etc.

The term "bread volume" as used herein is the volume of a baked good determined by using a laser scanner (e.g. Volscan Profiler ex Micro Stable System) to measure the volume as well as the specific volume. The term also includes the volume which is determined by measuring the length, the width and the height of certain baked goods.

The term "comprising" as used herein is synonymous with "including," "containing," or "characterized by," and is inclusive or open-ended and does not exclude additional, unrecited elements or method steps.

It is understood that aspects and embodiments of the invention described herein include "consisting" and/or "consisting essentially of" aspects and embodiments.

Throughout this disclosure, various aspects are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present disclosure will become apparent from the following specification taken in conjunction with the accompanying drawings.

In the following description, numerous specific details are set forth to provide a more thorough understanding of the present disclosure. However, it will be apparent to one of skill in the art that the methods of the present disclosure may be practiced without one or more of these specific details. In other instances, well-known features and procedures well known to those skilled in the art have not been described in order to avoid obscuring the disclosure.

Example 1: Lipase Expression and Purification

Expression

The enzymes were obtained by constructing expression plasmids containing the encoding polynucleotide sequences, transforming into *Pichia pastoris* (*Komagataella phaffii*) and growing the resulting expression strains in the following way. Fresh *Pichia pastoris* cells of the expression strains were obtained by spreading the glycerol stocks of sequence-confirmed strains onto Yeast extract Peptone Dextrose (YPD) agar plates containing Zeocin. After 2 days, starter seed cultures of the production strains were inoculated into 100 mL of Buffered Glycerol complex Medium (BMGY) medium using cells from these plates, and grown for 20-24 hours at 30° C. and 225-250 rpm. Seed cultures were scaled up by transferring suitable amounts into 2-4 L of BMMY medium in a baffled Fermentor. Fermentations were carried out at 30° C. and under 1100 rpm of agitation, supplied via flat-blade impellers, for 48-72 hours. After the initial batch-phase of fermentation, sterile-filtered Methanol was added as feed whenever the dissolved oxygen level in the culture dipped below 30%. Alternatively, feed was added every 3 hours at 0.5% v/v of the starting batch culture. The final fermentation broth was centrifuged at 7000×g for 30 mins at 4° C. to obtain the cell-free supernatant.

Purification

After filtering through cheese-cloth, the cell-free supernatants were ultrafiltered using a lab-scale tangential flow filtration (TFF) system with a molecular weight cut-off of 5 kD (SpectrumLabs). Samples were first concentrated 10-20× and then buffer-exchanged 5× into 50 mM HEPES pH 7.5.

A405 versus time and a standard PNP curve were used to calculate the enzyme activity per µg of enzyme. Similarly, the same assay was used to measure the activity: a) at different pH values (4.0-12.0), using the appropriate pH buffers and the PNP standard curve at that pH value; b) at different temperatures (25° C.-65° C.); c) in presence of different cofactors or salt concentrations (Ca2+, Mg2+, Zn2+, Na+, Cl—, EDTA); d) with different PNP substrates of various fatty acid chain length (C4-C18, Sigma). The results are shown in the table below.

| Lipase | Optimum | | | |
|---|---|---|---|---|
| | pH | Temperature ° C. | Cofactor | Fatty Acid Chain Length |
| Lip24 | 7.5-8.0 | 30-35 | Ca2+ | C8~C14~C16 > C4 > C18 |
| Lip49 | 8.5-10.5 | 35-40 | Mg2+ | C8 > C14 > C16~C18 > C4 |
| Lip61 | 8.5-10.0 | 30-50 | None | C8~C14 > C16 > C4~C18 |
| Lip62 | 8.5-10.5 | 25-40 | None | C8 > C14 > C16 > C4~C18 |
| Lip70 | 7.0 | 25 | None | C14 > C16~C8 > C4~C18 |
| Lip88 | 8.0-10.5 | 37-55 | None | C8 > C14 > C16 > C4~C18 |
| PANAMORE GOLDEN 2.2 | 8.5-10.0 | 30.0 | None | C10 |

The resultant retentate was centrifuged at 27000×g for 1 hour, and then sterile filtered through 0.2 µm filters to remove any production organisms or particulate matter. Total protein content of the final samples was determined using the Braford assay. Lipases were either kept in solution at −20° C. or lyophilized to form powder. In some cases, lipase solutions were sprayed on whole grain flour at 0.5 mg lipase per g flour, followed by drying at 40° C.

| Lipase | MW, kDa | pI | Origin |
|---|---|---|---|
| Lip24 | 50.73 | 4.38 | *Pseudomonas* sp |
| Lip49 | 35.6 | 4.58 | *Moritella marina* |
| Lip61 | 34.12 | 7.06 | *Fusarium solani* |
| Lip62 | 34.13 | 7.06 | *Fusarium solani* Jallouli et. al. "The galactolipase activity of *Fusarium solani* (phospho)lipase." Biochim Biophys Acta. 2015 Mar; 1851(3): 282-9. doi: 10.1016/j.bbalip.2014.12.010. Epub 2014 Dec. 18. PMID: 25529980 |
| Lip70 | 34.05 | 4.37 | *Colletotrichum fiorinae* |
| Lip88 | 34.19 | 7.12 | *Fusarium solani* U.S. Pat. No. 6,645,749-SEQ ID NO: 2 |
| PANAMORE GOLDEN 2.2 (DSM) | 36.9 | 5.19 | *Fusarium culmorum* WO2009106575-SEQ ID NO: 2 |
| LIPOPAN F (Novozymes) | 36.56 | 6.85 | *Fusarium oxysporum* WO1998026057-SEQ ID NO: 2 |

Example 2: Lipase Activity

Artificial Substrate

Lipase activity was determined using the artificial substrate p-nitrophenyl octanoate (C8-PNP, Sigma 21742), by detecting spectrophotometrically the chromogenic product p-nitrophenyl (PNP). C8-PNP was dissolved at 8 mM in 2-ethoxyethanol (Alfa Aesar), then diluted to 0.4 mM into 50 mM Hepes pH 7.5, 0.1 M NaCl (substrate assay buffer). Lipase stock was added to the substrate assay buffer at final concentrations between 0.1-1 µg/mL, then PNP formation was monitored immediately at 30° C. for 15 minutes by absorbance at 405 nm in a plate reader. The linear slope of Natural Lipid Substrates Alternatively, lipase activity was determined using natural lipid substrates and fluorogenic pH indicators detecting the pH change due to free fatty acid accumulation during hydrolysis. Natural substrates were isolated from flour as described below (MGDG=monogalactosyl diglyceride, DGDG=digalactosylactosyl diglyceride and TAGs=triacylglycerols) or PC from soy lecithin (PC=phosphatidyl choline). Natural substrate stock solutions were prepared at 5 mM final concentration in 0.25% Na-deoxycholate, using sonication (1-5 minutes) to disperse the lipids homogenously. To measure activity at pH 7.0-7.5, lipases were diluted at 0.1-1 µg/mL into 2 mM substrate, 0.1% Na-deoxycholate, 125 ng/mL fluorescein, 5 mM CaCl$_2$), 0.5 mM Hepes pH 7.5, followed by measuring fluorescence emission at 520 nm after excitation at 488 nm, at 30° C. for 15 minutes. The negative of linear slope of fluorescence versus time was used to calculate the lipase activity per µg enzyme. To measure activity at pH 7.5-8.0, lipases were diluted at 0.1-1 µg/mL into 2 mM substrate, 0.1% Na-deoxycholate, 250 ng/mL SNARF-1 (ThermoScientific S22801), 5 mM CaCl2), 1 mM Tris pH 8.0, followed by recording fluorescence emission at 580 nm after excitation at 514 nm, at 30° C. for 15 min. The linear slope of fluorescence versus time was used to calculate the lipase activity per µg enzyme.

Extraction of Natural Substrates from Flour or Soy Lecithin

Flour type 550 (Vogtmühlen Illertissen) (1000 g) was added to a 6 L 4-necked round-bottom flask along with 2500 mL of methanol. The contents of the flask were then stirred for 1.5 hours using a mechanical stirring blade at room temperature. After this period, the mixture was allowed to settle and the solvent was decanted and filtered through a silica gel/Celite pad by vacuum filtration. The remaining wheat flour was then re-extracted with a further 2500 mL methanol as before.

After extraction, the entire content of the flask was filtered through silica/Celite as before and washed thoroughly with methanol to minimize the loss of lipid products. Both extracts were combined and concentrated using the rotary evaporator to give a golden-brown syrup. The combined extract was then purified through a silica pad packed into a sintered glass funnel in order to separate the fatty, non-polar components from the polar components i.e. MGDG and DGDG. The silica gel pad was prepared by filling a 500 mL sintered glass funnel with silica and applying a vacuum to ensure complete packing of the pad. The raw material was then carefully added to the silica pad using a Pasteur pipette to ensure even distribution of the sample. The sample was the eluted with n-heptane:acetone (1:1, 2 L), n-heptane:acetone (1:4, 2 L), acetone (1 L) and acetone-methanol (4:1, 1 L). Fractions (1 L) were collected and, from TLC analysis, fraction 2 contained the bulk of the non-polar components (tri-, di-, monoglycerides), whereas, fractions 3-4 were observed to contain MGDG and fractions 5-6 contained DGDG. These fractions were separately concentrated using the rotary evaporator and further purified. The residue of fraction 2, (containing tri-, di-, monoglycerides) was purified performing a flash chromatography.

The column chromatography was run firstly using n-heptane followed by n-hepane:acetone (4:1) and n-hepane:acetone (1:1). The progress of the column chromatography was monitored via TLC analysis and the polarity of solvent system used for elution was increased accordingly. The fractions recovered from the column were then subjected to TLC analysis in order to evaluate which fractions could be combined in order to yield pure samples of tri-, di-, monoglycerides. The combined fractions were concentrated using the rotary evaporator. The residue of fractions 3-4, (MGDG containing fractions) was purified performing a flash chromatography. The column chromatography was run firstly using n-heptane followed by n-hepane:acetone (1:1). The progress of the column chromatography was monitored via TLC analysis and the polarity of solvent system used for elution was increased accordingly. The fractions recovered from the column were then subjected to TLC analysis in order to evaluate which fractions could be combined before concentration. The residue of fractions 5-6, (DGDG containing fractions) was purified performing a flash chromatography. The column chromatography was run using n-hepane:acetone (1:1), n-heptane:acetone (1:4) and finally using only acetone. The progress of the column chromatography was monitored via TLC analysis and the solvent system was change accordingly. The fractions recovered from the column were then subjected to TLC analysis in order to evaluate which fractions could be combined before concentration.

Phospholipids were purified to remove triglycerides and free fatty acids from soy lecithin by acetone extraction. Soy lecithin (10 g) was mixed with acetone (30 ml) in a 50 ml tube and mixed for 10 minutes. The resulting slurry was centrifuged at 4000×g for 5 minutes and the acetone phase was removed and discarded. The insoluble phospholipids were extracted 3 further times with fresh acetone.

| Abbreviation | Lipase Natural Substrates and Products |
|---|---|
| TAG | Triacyl glycerol |
| MGDG | Monogalactosyl diglyceride |
| DGDG | Digalactosyl diglyceride |
| NAPE | N-acylphosphatidyl ethanolamine |
| PC | Phosphatidyl choline |
| MAG | Monoacyl glycerol |
| DAG | Diacyl glycerol |
| FFA | Free fatty acid |
| MGMG | Monogalactosyl monoglyceride |
| DGMG | Digalactosyl monoglyceride |

| Lipase Name | Amino Acid SEQ ID No. | Nucleic Acid SEQ ID No. | Activity |
|---|---|---|---|
| LIP24 | 1 | 2 | Triacylglycerol lipase |
| LIP49 | 3 | 4 | Triacylglycerol lipase |
| LIP61 | 5 | 6 | Galactolipase > Phospholipase > Triacylglycerol lipase |
| LIP62 | 7 | 8 | Galactolipase > Phospholipase > Triacylglycerol lipase |
| LIP70 | 9 | 10 | Phospholipase > Galactolipase |
| LIP88 | 11 | 12 | Galactolipase > Phospholipase > Triacyglycerol lipase |
| PANAMORE GOLDEN 2.2 | N/A | N/A | Triacylglycerol lipase > Galactolipase > Phospholipase |

Lipolytic Activity in Dough Assessed by HPLC

Simplified doughs were used to test the activity of lipases on several substrates at once and under desired conditions. Dough was prepared from 10 g flour (US King Arthur flour for bread), 200 mg salt and 5.9 ml water and enzymes were supplemented at either 4 or 40 µg enzyme per dough. Doughs were mixed for 10 minutes by magnetic mixing then incubated in a humidity controlled chamber at 30° C. for a total of 60 minutes. Samples for analysis were taken from each dough at 10 and 60 minutes. For lipid analysis, 2 g wet dough sample was added to a vial containing 2 ml 0.1 N HCl and 10 ml 1-butanol. The dough was dispersed in the solvents to extract the lipids by shear homogenization (VWR 250 Homogenizer, 20×200 mm probe) for 30 seconds. The undissolved solids were then separated by centrifugation at 4000×g for 5 minutes at room temperature. The organic phase was removed and evaporated by centrifugal evaporation (Savant SpeedVac SC210A & Trap RVT5105), and the resulting solid was re-dissolved in isooctane:acetone:isopropanol (2:1:1) at $\frac{1}{10}$ the original volume for analysis. Lipids were separated by HPLC (Agilent 1100 series) with a silica gel column (Chromolith Performance Si 100-4.6 mm, Merck) and analyzed by ELSD (Agilent 1260 Infinity).

The chromatographic method for lipid separation was derived from Gerits, et. al. "Single run HPLC separation coupled to evaporative light scattering detection unravels wheat flour endogenous lipid redistribution during bread dough making" LWT-Food Science and Technology, 53 (2013) 426-433. Four samples, i.e. two time points and two enzyme doses, of each enzyme were used to determine if individual lipid classes increased, decreased or showed no change as a result of the enzyme treatment. Several of the enzymes tested show activity on a broad range of lipid classes as shown in the tables below and FIG. 1.

| Lipase | TAG | MAG | FFA | MGDG | MGMG | DGDG | DGMG | NAPE |
|---|---|---|---|---|---|---|---|---|
| Lip24 | − | + | + | 0 | 0 | 0 | 0 | 0 |
| Lip49 | − | + | + | 0 | 0 | 0 | 0 | 0 |
| Lip61 | − | − | + | − | + | − | 0 | − |
| Lip62 | − | + | + | − | + | − | + | − |
| Lip70 | 0 | − | + | − | + | − | + | − |
| Lip88 | − | + | + | − | + | − | + | − |
| PANAMORE GOLDEN 2.2 | − | − | + | − | + | − | + | − |

Legend
− Consumption of compound
+ Production of compound
0 No change in compound

Example 4: Baking Trials Pistolet Test

The baking performance of PANAMORE GOLDEN2.2, LIPOPAN F, LIP62, LIP61, LIP24, LIP49 dry lipase enzymes, and DATEM (LAMETOP 552) and also of PANAMORE GOLDEN2.2, LIPOPAN F, LIP62, LIP61, LIP24, LIP49, LIP88 lipase enzymes in solution, and DATEM (LAMETOP 552) were tested in a fast straight dough system, the Pistolet test. Flour type 550 (Vogtmühlen Illertissen) (2000 g), 120 g compressed yeast, 40 g salt, 30 g glucose, 22 g wheat starch, 120 ppm ascorbic acid, 5 ppm Nutrilife® AM 100 (fungal alpha-amylase), 200 ppm Nutrilife® CS 30 (fungal xylanase, cellulase, fungal alpha-amylase) and 1180 g water was mixed in a Kemper SP 15 spiral mixer for 5.5 minutes at speed 1 and 0.5 minutes at speed 2, to a final dough temperature of 28° C. After a resting of 12 minutes, the dough was scaled to a 1500 g piece, rounded and proofed for another 12 minutes. Afterwards the dough was divided and rounded into 30 pieces of 50 g each by using an automatic dough divider and rounder. Then the dough pieces were proofed for 35 (normal proof) and 45 (extended proof) minutes at 35° C. at relative humidity of 85%. After 12 minutes proofing time, a notch was pressed into the middle of the dough pieces. The proofed dough pieces were baked in a deck oven for 12 minutes at 240° C. with 15 seconds steam addition.

The effects on the dough properties and on the final baked goods, were compared to a negative control and to a reference containing 0.4% (based on flour weight) DATEM (Lametop® 552). PANAMORE GOLDEN2.2 was dosed at 14 ppm and LIPOPAN F was dosed at 40 ppm.

The volume effect was determined by measurement of the length, width, and height of 15 rolls in relation to the weight. The negative control is defined as 0%. Dough properties were evaluated manually by a master baker and described in comparison to the negative control.

The results of the dry lipases and lipases in solution are shown in the tables below.

| Dosage (μg lipase/g flour) | % Increase in Loaf Specific Volume Normal proof and dry Lipases (Pistolet) | | | | | | |
|---|---|---|---|---|---|---|---|
| | Lip62 | Lip61 | Lip24 | Lip49 | LIPOPAN F | PANAMORE GOLDEN 2.2 | DATEM LT552 |
| 0.17 | | | 6 | | | | |
| 0.33 | 6 | 5 | 9 | 1 | | | |
| 0.67 | 10 | 12 | 8 | 3 | 6 | 9 | |
| 1.34 | 11 | 10 | 5 | 3 | | | |
| 2.67 | | | | 6 | | | |
| 5.34 | | | | | | | |
| 0.40% | | | | 3 | | | 11 |

| Dosage (μg lipase/g flour) | % Increase in Loaf Specific Volume Extended proof and dry Lipases (Pistolet) | | | | | | |
|---|---|---|---|---|---|---|---|
| | Lip62 | Lip61 | Lip24 | Lip49 | LIPOPAN F | PANAMORE GOLDEN 2.2 | DATEM LT552 |
| 0.167 | | | 13 | | | | |
| 0.334 | 10 | 7 | 8 | 3 | | | |
| 0.668 | 14 | 13 | 10 | 5 | 10 | 12 | |
| 1.336 | 13 | 10 | 6 | 6 | | | |
| 2.672 | | | | 6 | | | |
| 5.344 | | | | | | | |
| 0.40% | | | | 1 | | | 14 |

| Dosage | % Increase in Loaf Specific Volume Normal proof and Lipases as solution (Pistolet) | | | | | | | |
|---|---|---|---|---|---|---|---|---|
| (µg lipase/g flour) | Lip62 | Lip61 | Lip88 | Lip49 | Lip70 | LIPOPAN F | PANAMORE GOLDEN 2.2 | DATEM LT552 |
| 0.17 | 4 | | | | | | | |
| 0.33 | 9 | 4 | | 3 | | | | |
| 0.67 | 14 | 12 | 4 | 3 | | 6 | 13 | |
| 1.34 | 13 | 11 | 6 | 6 | | | | |
| 2.67 | 10 | 7 | 7 | 6 | 0 | | | |
| 3.33 | | | 9 | | | | | |
| 5.34 | | 7 | | 6 | 5 | | | |
| 0.40% | | | | | | | | 14 |

| Dosage | % Increase in Loaf Specific Volume Extended proof and Lipases as solution (Pistolet) | | | | | | | |
|---|---|---|---|---|---|---|---|---|
| (µg lipase/g flour) | Lip62 | Lip61 | Lip88 | Lip49 | Lip70 | LIPOPAN F | PANAMORE GOLDEN 2.2 | DATEM LT552 |
| 0.17 | 3 | | | | | | | |
| 0.33 | 7 | 6 | | 8 | | | | |
| 0.67 | 13 | 9 | 3 | 10 | | 10 | 15 | |
| 1.34 | 12 | 12 | 7 | 10 | | | | |
| 2.67 | 13 | 8 | 12 | 14 | 4 | | | |
| 3.33 | | | 13 | | | | | |
| 5.34 | | 6 | | 11 | 12 | | | |
| 0.40% | | | | | | | | 20 |

| Dosage of Lip62 | DATEM | % Increase of Loaf Specific Volume (Pistolet) | |
|---|---|---|---|
| (µg/g flour) | (% of flour) | Normal Proof | Extended proof |
| 0 | 0 | 0 | 0 |
| 0 | 0.4 | 15 | 18 |
| 0.67 | 0 | 13 | 16 |
| 0.67 | 0.012 | 14 | 16 |
| 0.67 | 0.024 | 14 | 14 |
| 0.67 | 0.05 | 19 | 19 |
| 0 | 0 | 0 | 0 |
| 0 | 0.4 | 16 | 17 |
| 0.088 | 0.4 | 17 | 13 |
| 0.167 | 0.4 | 16 | 14 |
| 0.67 | 0.4 | 20 | 15 |

Example 5: Baking Trials Baguette

The baking performance of PANAMORE GOLDEN 2.2, LIPOPAN F, LIP62 enzymes, and DATEM (Lametop 552) were tested in French baguette. Prior to the baking trials, each enzyme was tested for activity, which can vary between different enzymes, then each enzyme was tested to determine the optimum dosage for that enzyme, and finally the enzymes were added at the optimum dosage. Flour (see flour type below) (1000 g), 25 g compressed yeast, 20 g salt, 60 ppm ascorbic acid, 3 ppm Nutrilife® AM 100 (fungal alpha-amylase), 150 ppm Nutrilife® CS 30 (fungal xylanase, cellulase, fungal alpha-amylase) and 650 g water was mixed in a Kemper SP 15 spiral mixer for 8 minutes at speed 1 and 4 minutes at speed 2, to a final dough temperature of 27° C. After a resting of 35 minutes, the dough was divided into 350 g pieces, rounded and proofed for 15 minutes. Afterwards the dough pieces were molded and proofed for 120 (normal proof) and 150 (extended proof) minutes at 27° C. at relative humidity of 75%. The proofed dough pieces were incised and baked in a deck oven for 25 minutes at 255° C., with steam addition after 30 seconds.

The effects on the dough properties and on the final baked goods, were compared to a negative control and to a reference containing 0.4% (based on flour) DATEM (Lametop® 552). Other controls were PANAMORE GOLDEN 2.2 (14 ppm) and LIPOPAN F (40 ppm). LIP62 was dosed at 60 ppm or 1.26 µg lipase/g flour.

The volume effect was determined by measuring the bread loavesvia a laser scanner (Micro Stable Systems Volscan). The negative control is defined as 0%. Dough properties were evaluated manually by a master baker and described in comparison to the negative control.

The results for the baguette using German flour (type 550 Vogtmühlen Illertissen) and Turkish flour baking trials are shown in the tables below.

| | % of Loaf Specific Volume Increase on German flour | |
|---|---|---|
| Baguette Baking Trials | Normal Proof | Extended proof |
| PANOMORE GOLDEN 2.2 | 15 | 20 |
| LIPOPAN F | 11 | 19 |
| Lip62 | 17 | 20 |
| DATEM (LT552) | 16 | 21 |

| Baguette Baking Trials | % of Loaf Specific Volume Increase on Turkish flour | |
|---|---|---|
| | Normal Proof | Extended proof |
| PANOMORE GOLDEN 2.2 | 10 | 15 |
| LIPOPAN F | 19 | 19 |
| Lip62 | 5 | 7 |
| DATEM (LT552) | 19 | 20 |

Example 6: Baking Trials Sweet Yeast Dough

The baking performance of PANAMORE GOLDEN 2.2, LIPOPAN F, LIP62 enzymes, and DATEM (Lametop 552) were tested in sweet yeast dough. Prior to the baking trials, each enzyme was tested for activity, which can vary between different enzymes, then each enzyme was tested to determine the optimum dosage for that enzyme, and finally the enzymes were added at the optimum dosage. Flour type 550 (Vogtmühlen Illertissen) (2000 g), 140 g compressed yeast, 30 g salt, 200 g sugar, 200 g margarine, 100 g eggs, 50 ppm ascorbic acid, 200 ppm Nutrilife® CS 30 (fungal xylanase, cellulase, fungal alpha-amylase) and 900 g water was mixed in a Kemper SP 15 spiral mixer for 6.5 minutes at speed 1 and 1.5 minutes at speed 2, to a final dough temperature of 26° C. After a resting of 25 minutes, the dough was scaled to a 1500 g piece, rounded and proofed for another 20 minutes. Afterwards the dough was divided and rounded into 30 pieces of 50 g each by using an automatic dough divider and rounder. Then 8 dough pieces were given into a baking tin and proofed for 50 minutes at 35° C. at relative humidity of 85%. The proofed dough pieces were baked in a deck oven for 35 minutes at 210° C./255° C. under and upper heat, with 15 seconds steam addition.

The effects on the dough properties and on the final baked goods, were compared to a negative control and to a reference containing 0.4% (based on flour weight) DATEM (Lametop® 552). Other controls were PANAMORE GOLDEN 2.2 (4 ppm) or LIPOPAN F (25 ppm). LIP62 was dosed at 25 ppm (0.52 µg lipase/g flour).

The volume effect was determined by measuring the bread loavesvia a laser scanner (Micro Stable Systems Volscan). The negative control is defined as 0%. Dough properties were evaluated manually by a master baker and described in comparison to the negative control.

The results of the sweet dough and sponge & dough baking trails are shown in the table below.

| | % Increase in Loaf Specific Volume on German Flour | | | |
|---|---|---|---|---|
| Application Type | PANAMORE GOLDEN 2.2 | LIPOPAN F | Lip62 | DATEM (LT552) |
| Sweet Yeast Dough | 11 | 13 | 13 | 20 |

Example 7: Baking Trials Sponge & Dough

The baking performance of PANAMORE GOLDEN 2.2, LIPOPAN F, LIP62 enzymes, and DATEM (Lametop 552) were tested in Sponge & Dough method. Prior to the baking trials, each enzyme was tested for activity, which can vary between different enzymes, then each enzyme was tested to determine the optimum dosage for that enzyme, and finally the enzymes were added at the optimum dosage. Flour type 550 (Vogtmühlen Illertissen) (1000 g), 5 g compressed yeast and 1000 g water was mixes and stored for 16 hours at either 4° C. or room temperature. Afterwards 1000 g of flour type 550 (Vogtmühlen Illertissen), 55 g compressed yeast, 40 g salt, 40 g sugar, 40 g margarine, 60 ppm ascorbic acid, 150 ppm Nutrilife® CS 30 (fungal xylanase, cellulase, fungal alpha-amylase) and 160 g water was mixed in a Kemper SP 15 spiral mixer for 5.5 minutes at speed 1 and 0.5 minutes at speed 2, to a final dough temperature of 27° C. After a resting of 15 minutes, the dough was divided into 450 g pieces, rounded and proofed for 10 minutes. Afterwards the dough pieces were molded, given into a baking tin and proofed for 80 minutes at 35° C. at relative humidity of 85%. The proofed dough pieces were baked in a deck oven for 30 minutes at 240° C./250° C. under and upper heat, with 15 seconds steam addition.

The effects on the dough properties and on the final baked goods, were compared to a negative control and to a reference containing 0.4% (based on flour weight) DATEM (Lametop® 552). Other controls were PANAMORE GOLDEN2.2 (7 ppm) or LIPOPAN F (50 ppm). LIP62 was dosed at 1.2 µg lipase/g flour.

The volume effect was determined by measuring the bread loaves via a laser scanner (Micro Stable Systems Volscan). The negative control is defined as 100%. Dough properties were evaluated manually by a master baker and described in comparison to the negative control.

| | % Increase in Loaf Specific Volume on German Flour | |
|---|---|---|
| Sponge & Dough Trial | 4° C. | Room temperature |
| Panamore Golden 2.2 | 2 | −1 |
| Lipopan F | 7 | 2 |
| LIP62 | 4 | 1 |
| DATEM (LT552) | 12 | 9 |

Example 8: Baking Trials Chorleywood Bread Process

The baking performance of PANAMORE GOLDEN 2.2, LIPOPAN F, LIP62 enzymes, and DATEM (Lametop 552) were tested in Chorleywood Bread Process. Prior to the baking trials, each enzyme was tested for activity, which can vary between different enzymes, then each enzyme was tested to determine the optimum dosage for that enzyme, and finally the enzymes were added at the optimum dosage. UK flour (Heygates Standard) (3000), 240 g compressed yeast, 45 g salt, 60 g improver (wheat flour, calcium sulfate, soy flour, ascorbic acid, bacterial xylanase, fungal alpha amylase) and 2010 g water was mixed in a pressure vacuum mixer (Pentagon K5) until an energy input of 58.3 kW/h was reached, to a final dough temperature of 30° C. The dough was divided, without resting time, into 450 g pieces, rounded and proofed for 2 minutes. Afterwards the dough pieces were molded, given into two baking tins and proofed for 55 minutes at 35° C. at relative humidity of 85%. Prior to baking one of the baking tins was used for a drop test, where the baking tin was dropped from a defined height. Then, the proofed dough pieces were baked in a deck oven for 25 minutes at 255° C./240° C. under and upper heat, with 15 seconds steam addition.

The effects on the dough properties and on the final baked goods, were compared to a negative control and to a reference containing 0.4% (based on flour weight) DATEM (Lametop® 552). Other controls were PANAMORE GOLDEN2.2 (18 ppm) or LIPOPAN F (30 ppm). LIP62 was dosed at 40 ppm or 0.8 µg lipase/g flour.

The volume effect was determined by measuring the bread loafs via a laser scanner (Micro Stable Systems Volscan). The negative control is defined as 100%. Dough properties were evaluated manually by a master baker and described in comparison to the negative control.

| Chorleywood Bread Process | % of Loaf Specific Volume Increase on UK flour | |
|---|---|---|
| | Normal Proof | After Drop Test |
| Panamore Golden 2.2 | 15 | 3 |
| Lipopan F | 17.5 | −7 |
| LIP62 | 16 | 37 |
| DATEM (LT552) | 34 | 23.5 |

The invention claimed is:

1. A method for increasing the volume of a baked product comprising:
   (a) providing a dough, wherein the dough is a composition comprising a flour, a salt, water, and yeast;
   (b) providing a lipase, and wherein the lipase is a polypeptide having the amino acid sequence of: SEQ ID NO:3, SEQ ID NO:5, SEQ ID NO:7, SEQ ID NO:9, or SEQ ID NO:11; and
   (c) combining the lipase of (b) with the dough of (a) and baking the combination to generate the baked product having an increased volume.

2. The method of claim 1, wherein the flour is selected from the group consisting of: almond flour, coconut flour, chia flour, corn flour, barley flour, spelt flour, soya flour, hemp flour, potato flour, quinoa, teff flour, rye flour, amaranth flour, arrowroot flour, chick pea (garbanzo) flour, cashew flour, flax meal, macadamia flour, millet flour, sorghum flour, rice flour, tapioca flour, and any combination thereof.

3. The method of claim 1, wherein the yeast is selected from the group consisting of: baker's yeast, cream yeast, compressed yeast, cake yeast, active dry yeast, instant yeast, osmotolerant yeasts, rapid-rise yeast, deactivated yeast, nutritional yeast, brewer's yeast, distiller's and wine yeast.

4. The method of claim 1, wherein the lipase is a variant polypeptide that is at least 97% identical to the amino acid sequence of SEQ ID NO:7 or at least 95% identical to an amino acid sequence selected from the group consisting of: SEQ ID NO:3, SEQ ID NO:5, SEQ ID NO:9 and SEQ ID NO:11, and wherein the variant polypeptide has lipase activity.

5. The method of claim 1, wherein the lipase is a polypeptide encoded by a nucleic acid sequence that encodes the amino acid sequence selected from the group consisting of: SEQ ID NO:4, SEQ ID NO:6, SEQ ID NO:8, SEQ ID NO:10 and SEQ ID NO:12.

6. The method of claim 1, further comprising the addition of a second enzyme.

7. The method of claim 6, wherein the second enzyme comprises a second lipase, an Alpha-amylase; a Glucan 1,4-alpha-maltotetraohydrolase; an exo-maltotetraohydrolase; a G4-amylase; a Glucan 1,4-alpha-maltohydrolase; a maltogenic alpha-amylase; a cyclodextrin glucanotransferase; a CGTase; a glucoamylase; an Endo-1,4-beta-xylanase; a xylanase; a cellulase; an Oxidoreductases; a Phospholipase A1; a Phospholipase A2; a Phospholipase C; a Phospholipase D; a Galactolipase, triacylglycerol lipase, an arabinofuranosidase, a transglutaminase, a pectinase, a pectate lyase, a protease, or any combination thereof.

8. The method of claim 1, wherein the lipase is active at a range from pH 4.0 to pH 12.0.

9. The method of claim 1, wherein the lipase is active at a temperature range from 20° to 60° C.

10. A method for increasing the volume of a baked product without the addition of diacetyl tartaric acid esters of monoglycerides (DATEM) comprising:
   (a) providing a dough, wherein the dough is a composition comprising a flour, a salt, water, and yeast;
   (b) providing a lipase, and wherein the lipase is a polypeptide having the amino acid sequence of: SEQ ID NO:3, SEQ ID NO:5, SEQ ID NO:7, SEQ ID NO:9, or SEQ ID NO:11; and
   (c) combining the lipase of (b) with the dough of (a) without the addition of DATEM and baking the combination to generate the baked product having an increased volume.

11. The method of claim 10, wherein the flour is selected from the group consisting of: almond flour, coconut flour, chia flour, corn flour, barley flour, spelt flour, soya flour, hemp flour, potato flour, quinoa, teff flour, rye flour, amaranth flour, arrowroot flour, chick pea (garbanzo) flour, cashew flour, flax meal, macadamia flour, millet flour, sorghum flour, rice flour, tapioca flour, and any combination thereof.

12. The method of claim 10, wherein the yeast is selected from the group consisting of: baker's yeast, cream yeast, compressed yeast, cake yeast, active dry yeast, instant yeast, osmotolerant yeasts, rapid-rise yeast, deactivated yeast, nutritional yeast, brewer's yeast, distiller's and wine yeast.

13. The method of claim 10, wherein the lipase is a polypeptide having an amino acid sequence selected from the group consisting of: SEQ ID NO:3, SEQ ID NO:5, SEQ ID NO:7, SEQ ID NO:9 and SEQ ID NO:11.

14. The method of claim 10, wherein the lipase is a variant polypeptide that is at least 97% identical to the amino acid sequence of SEQ ID NO:7 or at least 95% identical to an amino acid sequence selected from the group consisting of: SEQ ID NO:3, SEQ ID NO:5, SEQ ID NO:9 and SEQ ID NO:11, and wherein the variant polypeptide has lipase activity.

15. The method of claim 10, wherein the lipase is a polypeptide encoded by a nucleic acid sequence that encodes the amino acid sequence selected from the group consisting of: SEQ ID NO:3, SEQ ID NO:5, SEQ ID NO:7, SEQ ID NO:9 and SEQ ID NO:11.

16. The method of claim 10, further comprising the addition of a second enzyme.

17. The method of claim 10, wherein the second enzyme comprises a second lipase, an Alpha-amylase; a Glucan 1,4-alpha-maltotetraohydrolase; an exo-maltotetraohydrolase;

a G4-amylase; a Glucan 1,4-alpha-maltohydrolase; a maltogenic alpha-amylase; a cyclodextrin glucanotransferase; a CGTase; a glucoamylase; an Endo-1,4-beta-xylanase; a xylanase; a cellulase; an Oxidoreductases; a Phospholipase A1; a Phospholipase A2; a Phospholipase C; a Phospholipase D; a Galactolipase, triacylglycerol lipase, an arabinofuranosidase, a transglutaminase, a pectinase, a pectate lyase, a protease, or any combination thereof.

18. The method of claim 10, wherein the lipase is active at a range from pH 4.0 to pH 12.0.

19. The method of claim 10, wherein the lipase is active at a temperature range from 20° C. to 60° C.

* * * * *

SEQUENCE LISTING

<160> NUMBER OF SEQ ID NOS: 12

<210> SEQ ID NO 1
<211> LENGTH: 474
<212> TYPE: PRT
<213> ORGANISM: Pseudomonas

<400> SEQUENCE: 1

```
Met Gly Val Phe Asp Tyr Lys Asn Leu Gly Ala Glu Gly Ser Lys Ala
1               5                   10                  15

Leu Phe Ala Asp Ala Met Ala Ile Thr Leu Tyr Thr Tyr His Asn Leu
            20                  25                  30

Asp Asn Gly Phe Ala Val Gly Tyr Gln His Asn Gly Leu Gly Val Gly
        35                  40                  45

Leu Pro Ala Thr Leu Val Gly Ala Leu Leu Gly Ser Thr Asp Ser Gln
    50                  55                  60

Gly Val Ile Pro Gly Ile Pro Trp Asn Pro Asp Ser Glu Lys Ala Ala
65                  70                  75                  80

Leu Glu Ala Val Gln Lys Ala Gly Trp Thr Pro Ile Ser Ala Ser Thr
                85                  90                  95

Leu Gly Tyr Thr Gly Lys Val Asp Ala Arg Gly Thr Phe Phe Gly Glu
            100                 105                 110

Lys Ala Gly Tyr Thr Thr Ala Gln Val Glu Val Leu Gly Lys Tyr Asp
        115                 120                 125

Asp Ala Gly Gln Leu Gln Glu Ile Gly Ile Gly Phe Arg Gly Thr Ser
    130                 135                 140

Gly Pro Arg Glu Thr Leu Ile Thr Asp Ser Ile Gly Asp Leu Val Ser
145                 150                 155                 160

Asp Leu Leu Ala Ala Leu Gly Pro Lys Asp Tyr Ala Lys Asn Tyr Ala
                165                 170                 175

Gly Glu Ala Phe Gly Gly Leu Leu Lys Ser Val Ala Glu Tyr Ala Ala
            180                 185                 190

Ala His Gly Leu Ser Gly Gln Asp Val Leu Val Ser Gly His Ser Leu
        195                 200                 205

Gly Gly Leu Ala Val Asn Ser Met Ala Asp Leu Ser Asp Ala Lys Trp
    210                 215                 220

Ser Gly Phe Tyr Lys Asp Ala Asn Tyr Leu Ala Tyr Ala Ser Pro Thr
225                 230                 235                 240

Gln Ser Ala Ser Asp Lys Val Leu Asn Ile Gly Tyr Glu Asn Asp Pro
                245                 250                 255
```

| | | | | | | | | | | | |
|---|---|---|---|---|---|---|---|---|---|---|---|
|Val|Phe|Arg|Ala|Leu|Asp|Gly|Ser|Ser|Ala|Asn|Leu|Ser|Thr|Leu|Gly|
| | | |260| | | |265| | | |270| | | | |

Val His Asp Lys Pro His Glu Ser Thr Thr Asp Asn Ile Val Ser Phe
                275                       280                       285

Asn Asp His Tyr Ala Ser Thr Leu Trp Asn Val Leu Pro Phe Ser Ile
290                         295                             300

Ala Asn Leu Pro Thr Trp Ile Ser His Leu Pro Thr Gly Tyr Gly Asp
305                     310                      315                320

Gly Met Gly Arg Ile Leu Glu Ser Gly Phe Tyr Glu Gln Met Thr Arg
                325                       330                     335

Asp Ser Thr Ile Ile Val Ala Asn Leu Ser Asp Pro Ala Arg Ala Thr
            340                     345                    350

Thr Trp Val Gln Asp Leu Asn Arg Asn Ala Glu Pro His Thr Gly Asp
          355                     360                   365

Thr Phe Ile Ile Gly Ser Asp Gly Asp Leu Ile Leu Gly Gly Lys
       370                 375                380

Gly Ala Asp Phe Ile Glu Gly Gly Lys Gly Asn Asp Thr Ile Arg Asp
385                     390                     395               400

Ser Ser Gly His Asn Thr Phe Leu Phe Ser Gly Gln Phe Gly Gln Asp
                405                     410                   415

Arg Ile Ile Gly Tyr Gln Pro Thr Asp Lys Leu Val Phe Gln Gly Val
            420                     425                    430

Ala Gly Ser Gly Asp Tyr Arg Asp His Ala Lys Val Gly Gly Asp
                  435                   440               445

Thr Val Ile Ser Phe Gly Ala Asp Ser Val Thr Leu Val Gly Val Ser
450                     455                     460

Gly Val Leu Gly Glu Gly Val Val Ile Gly
465                     470

<210> SEQ ID NO 2
<211> LENGTH: 1422
<212> TYPE: DNA
<213> ORGANISM: Pseudomonas

<400> SEQUENCE: 2

| | | |
|---|---|---|
|atgggtgtgt tgactataa aaaccttggg gccgagggct ccaaggcctt gtttgccgat|60|
|gccatggcga tcacgttgta tacctaccac aacctggata acggctttgc cgtgggctac|120|
|cagcacaatg gcctgggcgt cggcttgccg gctactctgg tcggcgcatt gctcggcagt|180|
|acggactccc agggtgtgat cccaggcatt ccctggaacc cggattcgga gaaggccgcg|240|
|ctcgaagcgg tgcagaaggc cggctggacg cccatcagcg ccagcaccct cgggtatacc|300|
|ggcaaggtcg acgcccgggg cacgttcttc ggcgaaaagg ccggctacac cacgcccag|360|
|gtcgaggtgc tgggcaagta cgatgacgcg ggccagttgc aggaaatcgg catcggtttt|420|
|cgcggcacgt ctggcccaag ggaaacactg atcaccgact ccatcggcga tctggtcagc|480|
|gacctgcttg ctgcgctggg tcccaaggat tacgcaaaga actacgccgg cgaagcattc|540|
|ggcggcttgc tcaagagcgt cgccgagtat gcggcggccc acgtctcag cggccaggat|600|
|gtgctggtca cgccatag cctcggcggc ctggcggtca acagcatggc cgacttgagc|660|
|gacgccaagt ggtccgggtt ctataaggac gccaactact ggcctacgc ctcaccgacc|720|
|cagagtgcca cgacaaggt gcttaatatc ggctacgaaa acgacccggt gttccgcgcc|780|
|ctggacggct catccgccaa cctgtcgacg ctcggtgttc acgacaaacc ccacgagtcc|840|
|accactgaca acattgtcag cttcaacgat cactacgcct cgaccctgtg gaatgtgctg|900|

```
ccgttttcca tcgccaatct gccgacttgg atctcgcact tgccgaccgg ctacggcgac    960
ggcatggggc gcattctgga gtccgggttc tatgaacaga tgacccggga ctcgacgatt   1020
atcgtggcca atctatccga cccggcacgg gccaccactt gggttcagga cctgaaccgc   1080
aacgccgaac gcacacagg cgacactttc atcattggca gcgatggcga tgatctgatc   1140
ctgggcggca agggcgcgga ctttatcgaa ggcggcaagg gcaatgacac gatccgcgac   1200
agcagcgggc ataacacctt tttgttcagc ggccagtttg gcaggatcg gattatcggt   1260 tatcagccga cggataaact cgtgttccag ggtgtggcgg gcagcgggga ttaccgtgat   1320
cacgccaagg tggtgggtgg ggatacggtg atcagtttcg gggcggattc ggtgacgtta   1380
gtgggcgtta gcggggtgtt gggggagggg gttgtgatcg gc                      1422
```

<210> SEQ ID NO 3
<211> LENGTH: 334
<212> TYPE: PRT
<213> ORGANISM: Moritella marina

<400> SEQUENCE: 3

```
Met Phe Lys Ile Asn Arg Ile Leu Phe Ser Val Phe Ala Ile Met
1               5                  10                  15

Cys Phe Met Val Ala Pro Ala Gln Ala Asp Ser Ser Gly Ile Asp Arg
            20                  25                  30

Ser Gly Lys Thr Lys Tyr Pro Val Leu Val His Gly Leu Ser Gly
        35                  40                  45

Phe Asp Ser Val Phe Ala Asp Tyr Phe Tyr Gly Val Lys Gly Ala Leu
    50                  55                  60

Ala Ser Val Gly Ser Thr Glu Val Tyr Thr Pro Leu Ile Thr Gly Phe
65                  70                  75                  80

Asn Thr Ser Glu Val Arg Gly Glu Gln Leu Leu Ser Tyr Leu Glu Asp
                85                  90                  95

Leu Lys Ala Val Thr Gly Ala Gln Lys Phe Asn Leu Ile Gly His Ser
            100                 105                 110

Gln Gly Gly Ile Asp Ala Arg Tyr Val Ala Ser Val Arg Pro Asp Leu
        115                 120                 125

Val Ala Ser Val Thr Ser Val Gly Ser Pro His Phe Gly Ser Gly Thr
    130                 135                 140

Ala Asp Leu Val Lys Asp Ser Pro Leu Glu Gly Ala Ala Met Asp Ile
145                 150                 155                 160

Gly Asn Ala Val Gly Ala Leu Leu Ala Ala Val Thr Gly Asp Thr Ser
                165                 170                 175

Gln Gln Val Asp Ala Met Gly Ala Leu Glu Ala Leu Asn Ser Ala Asp
            180                 185                 190

Ala Ala Val Phe Asn Ala Lys Tyr Pro Glu Gly Leu Arg Gln Gly Asp
        195                 200                 205

Cys Gln Glu Thr Pro Arg Tyr Asn Ala Gly Ser Trp Trp Pro Asn
    210                 215                 220

Trp Val Tyr Asp Tyr Ser Val Asn Asp Gly Glu His Asn Val Asn Gly
225                 230                 235                 240

Val Ala Tyr Tyr Ser Trp Gly Gly Thr Tyr Asn Pro Val Phe Asn Ser
                245                 250                 255

Asn Val Leu Asp Leu Ala Asp Gly Leu Leu Ala Ala Tyr Leu Thr
            260                 265                 270

Ile Asp Glu Ser Asn Asp Gly Val Val Gly Arg Cys Ser Thr His Leu
```

Gly Gln Val Ile Arg Asp Asp Tyr Thr Met Asn His Ala Asp Glu Ile
            275                 280                 285

Asn Gly Met Phe Gly Leu Arg Gly Leu Gly Thr Thr Ser Pro Leu Pro
    290                 295                 300

Leu Tyr Val Glu His Ala Arg Arg Leu Thr Arg Ala Gly Leu
305                 310                 315                 320
                325                 330

<210> SEQ ID NO 4
<211> LENGTH: 1005
<212> TYPE: DNA
<213> ORGANISM: Moritella marina

<400> SEQUENCE: 4

| | | | | | |
|---|---|---|---|---|---|
| atgtttaaaa | taaatcggat | tttattctca | gtctttgtcg | ccatcatgtg | ttttatggtt | 60 |
| gcaccggcac | aagcagatag | ttcaggaata | gatagatcag | gaaaaacaaa | atacccggta | 120 |
| gttttagtac | atggccttc | aggttttgac | agcgtgtttg | cagattattt | ttatggcgta | 180 |
| aaaggcgcgt | tagccagtgt | tggttctacc | gaggtatata | caccactgat | tacgggattt | 240 |
| aatacgagtg | aagtacgtgg | agagcaattg | ctgagttatc | tggaggattt | gaaagcggtc | 300 |
| accggtgcgc | aaaaatttaa | cctaataggc | cattctcaag | gtggtatcga | tgcacgttac | 360 |
| gtggcttccg | ttcgaccaga | cttagtcgcg | tcggttactt | ctgttggttc | tccccatttt | 420 |
| ggctctggca | ctgcagattt | agttaaagat | tcgccactcg | aaggtgcagc | tatggatata | 480 |
| ggtaatgctg | tgggtgcact | tttagcggct | gttaccgggg | atacatcgca | gcaggtagat | 540 |
| gccatggggg | ctcttgaagc | attaaattca | gcggatgcgg | cggttttcaa | tgctaaatat | 600 |
| cctgaaggt | tacgtcaggg | ggattgtcag | gaaaccctc | gttataatgc | cggttcttgg | 660 |
| tggtggccaa | attgggttta | tgattactct | gttaatgatg | gtgagcacaa | cgtaaatggt | 720 |
| gtggcttatt | actcatgggg | aggaacttac | aaccctgtgt | taattcaaa | tgtgctggat | 780 |
| ctggctgatg | gtttgttagc | ggcagcctat | ttgactatcg | atgagtcaaa | cgatggtgtc | 840 |
| gttggccgct | gctcaacgca | tctgggccag | gttattcgtg | atgactatac | catgaatcac | 900 |
| gcagacgaga | taaatggaat | gtttggttta | cgtggtttgg | gtacaacgag | cccattacct | 960 |
| ttatatgtgg | agcatgcaag | acgtctgact | cgtgcgggtt | tgtaa | | 1005 |

<210> SEQ ID NO 5
<211> LENGTH: 317
<212> TYPE: PRT
<213> ORGANISM: Fusarium solani

<400> SEQUENCE: 5

Ala Ile Thr Ala Ser Thr Leu Asp Tyr Glu Asn Phe Lys Phe Tyr Ile
1               5                   10                  15

Gln His Gly Ala Ala Tyr Cys Asn Ser Glu Thr Ala Ser Gly Glu
            20                  25                  30

Lys Ile Thr Cys Ser Asp Ser Ala Cys Lys Val Val Glu Ala Asn Asn
            35                  40                  45

Val Val Val Val Ala Ser Phe Val Gly Thr Gly Thr Gly Ile Gly Gly
        50                  55                  60

Tyr Val Ser Thr Asp Asp Ile Arg Lys Glu Ile Val Leu Ser Ile Arg
65                  70                  75                  80

Gly Ser Ser Asn Ile Arg Asn Trp Leu Thr Asn Val Asp Phe Gly Gln
                85                  90                  95

```
Ser Gly Cys Ser Tyr Val Lys Asp Cys Gly Val His Thr Gly Phe Arg
            100                 105                 110
Asn Ala Trp Asp Glu Ile Ala Gln Arg Ala Arg Asp Ala Ile Ala Lys
        115                 120                 125
Ala Arg Ala Lys Asn Pro Ser Tyr Lys Val Ile Ala Thr Gly His Ser
130                 135                 140
Leu Gly Gly Ala Val Ala Thr Leu Gly Gly Ala Asp Leu Arg Ser Lys
145                 150                 155                 160
Gly Thr Ala Val Asp Ile Phe Thr Phe Gly Ala Pro Arg Val Gly Asn
                165                 170                 175
Ala Glu Leu Ser Ala Phe Ile Thr Ser Gln Ala Gly Gly Glu Phe Arg
            180                 185                 190
Val Thr His Gly Arg Asp Pro Val Pro Arg Leu Pro Pro Ile Val Phe
        195                 200                 205
Gly Tyr Arg His Thr Ser Pro Glu Tyr Trp Leu Ala Gly Gly Ala Ser
210                 215                 220
Thr Lys Ile Asp Tyr Ser Val Asn Asp Ile Glu Val Cys Glu Gly Ser
225                 230                 235                 240
Ala Asn Leu Ala Cys Asn Gly Gly Thr Leu Gly Leu Asp Ile Val Ala
                245                 250                 255
His Leu Arg Tyr Phe Gln Asn Thr Asp Ala Cys Thr Ala Gly Gly Ile
            260                 265                 270
Ser Trp Lys Arg Gly Asp Lys Ala Lys Arg Asn Glu Ile Pro Lys Arg
        275                 280                 285
Arg Asp Ser Met Thr Asp Glu Glu Leu Glu Arg Lys Leu Asn Asp Tyr
290                 295                 300
Val Ala Met Asp Lys Glu Tyr Val Glu Ser Asn Lys Met
305                 310                 315

<210> SEQ ID NO 6
<211> LENGTH: 954
<212> TYPE: DNA
<213> ORGANISM: Fusarium solani

<400> SEQUENCE: 6
gccattactg cttctacttt agattatgaa aatttcaaat tttacatcca acacggtgcc      60
gctgcttact gtaattctga gactgcctct ggagaaaaga taacttgttc cgactccgct     120
tgtaaggttg ttgaggccaa caacgtcgtt gttgtggcct ccttcgttgg tactggtact     180
ggaattggtg gttacgtttc tactgatgac attcgtaaag aaatcgttct atccattaga     240
ggtagttcta acattagaaa ctggttaact aacgtcgatt tcggtcaatc tggttgttct     300
tacgtcaagg attgtggtgt tcacactggt ttcagaaacg catgggacga aatcgctcag     360
agagcccgtg atgctattgc aaaggccaga gctaaaaacc catcttacaa ggttattgca     420
actggtcact ctctaggagg tgcagttgct actttaggtg gtgccgactt gcgatcaaag     480
ggtaccgccg ttgacatctt taccttcgga gctcctcgtg tcgggaacgc cgagcttagc     540
gctttcatca aagtcaagc tggtggtgaa ttcagagtga ctcacggtag agaccctgtt     600
cctagactgc ctccaatcgt gtttggctac agacatactt ccccagagta ctggctagcc     660
ggtggtgcct ccactaagat cgattattct gttaatgata tcgaagtctg tgagggttcc     720
gccaacttgg cttgtaatgg tggtactttg gtctagata ttgtcgctca cttgagatac     780
tttcaaaaca ccgatgcctg taccgctggt ggaatttctt ggaagagagg agataaggct     840
aaacgtaacg agattcctaa gaagagagac tccatgaccg atgaggagtt agagagaaag     900
```
ctcaacgact acgtggctat ggacaaggag tacgtagaat ccaacaagat gtaa      954

<210> SEQ ID NO 7
<211> LENGTH: 317
<212> TYPE: PRT
<213> ORGANISM: Fusarium solani

<400> SEQUENCE: 7

```
Ala Ile Thr Ala Ser Gln Leu Asp Tyr Glu Asn Phe Lys Phe Tyr Ile
1               5                   10                  15

Gln His Gly Ala Ala Tyr Cys Asn Ser Glu Thr Ala Ser Gly Gln
            20                  25                  30

Lys Ile Thr Cys Ser Asp Asn Gly Cys Lys Gly Val Glu Ala Asn Asn
        35                  40                  45

Ala Ile Ile Val Ala Ser Phe Val Gly Lys Gly Thr Gly Ile Gly Gly
    50                  55                  60

Tyr Val Ser Thr Asp Asn Val Arg Lys Glu Ile Val Leu Ser Ile Arg
65                  70                  75                  80

Gly Ser Ser Asn Ile Arg Asn Trp Leu Thr Asn Val Asp Phe Gly Gln
                85                  90                  95

Ser Ser Cys Ser Tyr Val Arg Asp Cys Gly Val His Thr Gly Phe Arg
            100                 105                 110

Asn Ala Trp Asp Glu Ile Ala Gln Arg Ala Arg Asp Ala Val Ala Lys
        115                 120                 125

Ala Arg Thr Met Asn Pro Ser Tyr Lys Val Ile Ala Thr Gly His Ser
    130                 135                 140

Leu Gly Gly Ala Val Ala Thr Leu Gly Ala Ala Asp Leu Arg Ser Lys
145                 150                 155                 160

Gly Thr Ala Val Asp Ile Phe Thr Phe Gly Ala Pro Arg Val Gly Asn
                165                 170                 175

Ala Glu Leu Ser Ala Phe Ile Thr Ala Gln Ala Gly Gly Glu Phe Arg
            180                 185                 190

Val Thr His Gly Arg Asp Pro Val Pro Arg Leu Pro Pro Ile Val Phe
        195                 200                 205

Gly Tyr Arg His Thr Ser Pro Glu Tyr Trp Leu Ala Gly Gly Ala Ser
    210                 215                 220

Thr Lys Thr Asp Tyr Thr Val Asn Asp Ile Lys Val Cys Glu Gly Ala
225                 230                 235                 240

Ala Asn Leu Ala Cys Asn Gly Gly Thr Leu Gly Leu Asp Ile Ile Ala
                245                 250                 255

His Leu Arg Tyr Phe Gln Asp Thr Asp Ala Cys Thr Ala Gly Gly Ile
            260                 265                 270

Ser Trp Lys Arg Gly Asp Lys Ala Lys Arg Asp Glu Ile Pro Lys Arg
        275                 280                 285

Gln Glu Gly Met Thr Asp Glu Glu Leu Glu Gln Lys Leu Asn Asp Tyr
    290                 295                 300

Val Ala Met Asp Lys Glu Tyr Val Glu Ser Asn Lys Met
305                 310                 315
```

<210> SEQ ID NO 8
<211> LENGTH: 954
<212> TYPE: DNA
<213> ORGANISM: Fusarium solani

<400> SEQUENCE: 8

-continued

```
gccattactg cttctcaatt ggactacgaa aacttcaagt tttacatcca gcacggtgcc      60
gctgcttact gtaactccga aactgcctct ggtcaaaaga tcacttgttc cgacaacggt     120
tgcaaaggtg tcgaagctaa caacgctatt attgtcgcct ctttcgttgg aaaaggtact     180
ggtattggtg gttacgtttc tactgataac gttagaaagg agatcgtttt gtctattaga     240
ggttcttcca acattcgtaa ctggttgact aacgtcgact tcggacaatc ctcttgttct     300
tacgttagag attgtggagt tcacactggt ttcagaaatg cttgggacga gattgcccaa     360
agagctagag acgctgtcgc taaagctaga actatgaacc catcttacaa ggttatcgct     420
actggtcact ctttgggtgg tgctgttgcc actttgggtg ctgctgattt gagatccaag     480
ggtactgccg tcgatatctt tacttttggt gccccaagag ttggtaacgc tgagttgtcc     540
gctttcatca ctgctcaggc tggtggtgag ttcagagtta ctcacggacg tgatccagtt     600
ccacgtttgc cacctatcgt cttcggttac agacacacct ctccagagta ctggttggct     660
ggtggtgctt ccaccaagac tgattatact gttaacgata tcaaggtttg tgaaggtgcc     720
gctaacttgg cctgtaatgg tggtactttg ggattggata tcattgctca tttgagatac     780
ttccaagaca ctgacgcctg tactgctggt ggtatctcct ggaagagagg tgacaaagct     840
aagagagatg agattccaaa aagacaagaa ggaatgactg atgaggagtt ggaacaaaaa     900
ctgaacgact atgtcgccat ggataaggag tacgttgagt ccaacaagat gtaa           954
```

<210> SEQ ID NO 9
<211> LENGTH: 322
<212> TYPE: PRT
<213> ORGANISM: Colletotrichum fiorinae

<400> SEQUENCE: 9

```
Ser Pro Leu Leu Asp Ala Arg Ala Pro Val Ala Ala Leu Asp Glu Arg
1               5                   10                  15

Ala Val Thr Val Ser Ser Ala Asp Leu Ser Asn Phe Glu Tyr Tyr Val
            20                  25                  30

Gln Met Val Ala Ala Thr Ser Cys Asn Ser Glu Ala Ala Ala Gly Ala
        35                  40                  45

Ser Ile Thr Cys Ser Ala Asp Ala Cys Pro Asp Val Thr Ala Asn Gly
    50                  55                  60

Gly Lys Ile Val Gly Thr Phe Ser Gly Leu Val Ser Gly Leu Glu Gly
65                  70                  75                  80

Phe Val Ala Thr Asp Pro Val Arg Lys Asn Ile Val Ile Ala Ile Arg
                85                  90                  95

Gly Ser Ser Asn Val Arg Asn Trp Ile Thr Asn Ile Leu Phe Gly Phe
            100                 105                 110

Asp Asp Cys Asp Phe Val Asp Gly Cys Lys Val His Thr Gly Phe Ala
        115                 120                 125

Asn Gly Trp Asp Glu Ile Lys Asp Ser Leu Leu Ala Ser Val Lys Ser
    130                 135                 140

Ala Lys Ala Ala Asn Pro Ser Tyr Thr Ile Val Gly Thr Gly His Ser
145                 150                 155                 160

Leu Gly Gly Ala Val Val Thr Ile Ala Ala Ala Asp Leu Arg Arg Asp
                165                 170                 175

Gly Tyr Pro Val Asp Ile Tyr Thr Tyr Gly Ser Pro Arg Val Gly Asn
            180                 185                 190

Ala Ala Phe Thr Asn Phe Val Thr Ala Gln Ala Gly Ala Glu Tyr Arg
        195                 200                 205
```

```
Val Thr His Val Asp Asp Pro Val Pro Arg Leu Pro Pro Ile Leu Phe
    210                 215                 220

Gly Tyr Arg His Thr Ser Pro Glu Tyr Trp Leu Ser Thr Gly Asn Ala
225                 230                 235                 240

Thr Thr Val Asp Tyr Ala Val Ala Asp Ile Lys Val Cys Glu Gly Ala
                245                 250                 255

Ala Asn Thr Lys Cys Asn Gly Gly Thr Phe Gly Leu Asp Val Asp Ala
                260                 265                 270

His Leu Tyr Tyr Leu Arg Arg Thr Gly Ala Cys Ser Thr Asp Gly Phe
                275                 280                 285

Gly Ile Lys Glu Arg Glu Asp Ile Ser Asp Glu Asp Leu Ala Ala
290                 295                 300

Arg Leu Thr Ala Trp Ala Gln Gln Asp Ile Glu Tyr Ala Ala Ser Leu
305                 310                 315                 320

Glu Glu
```

<210> SEQ ID NO 10
<211> LENGTH: 966
<212> TYPE: DNA
<213> ORGANISM: Colletotrichum fiorinae

<400> SEQUENCE: 10

```
tctccattgt tggatgcccg tgccccagtc gctgctctgg atgaacgtgc tgttactgtt      60
tcttctgctg atctttccaa ttttgagtac tacgtccaga tggttgctgc tacctcttgt     120
aattctgaag ctgccgccgg tgcttctatt acctgttctg ctgacgcttg tcctgacgtt     180
actgctaatg gtggaaagat cgttggtacc ttctccggat tggtttctgg tcttgagggt     240
ttcgtcgcca ctgaccctgt tagaaagaat attgttattg ctattagagg ttcctctaat     300
gttagaaatt ggattactaa tatcttgttc ggttttgacg actgtgactt cgttgacggt     360
tgtaaggtcc ataccggatt cgctaacggt tgggacgaaa tcaaggactc cttgttggct     420
tccgtcaagt ctgctaaggc tgccaaccct tcttacacta tcgttggtac cggacactct     480
ttgggtggtg ccgttgttac tattgctgct gccgatttga aagagacgg ttaccctgtc     540
gacatctaca cttatggatc tccaagagtt ggtaacgctg ctttcaccaa ctttgttacc     600
gctcaggctg gtgctgagta cagagttacc cacgtcgatg acccagttcc aagactgcca     660
cctatcttgt tcggatacag acacacctcc ccagagtact ggctgtccac cggaaacgct     720
actactgtcg actacgctgt cgccgacatt aaggtctgtg aaggtgctgc taacaccaag     780
tgtaacggtg gtactttggg tttggacgtc gacgctcacc tttactactt gcgtagaact     840
ggtgcctgtt ccactgatgg attcggtatt aaagagcgtg aggaagatat ttctgacgag     900
gacttggccg ctagactgac tgcttgggcc aacaggaca ttgaatatgc tgcttctttg     960
gaggag                                                                966
```

<210> SEQ ID NO 11
<211> LENGTH: 317
<212> TYPE: PRT
<213> ORGANISM: Fusarium solani

<400> SEQUENCE: 11

```
Ala Ile Thr Ala Ser Gln Leu Asp Tyr Glu Asn Phe Lys Phe Tyr Ile
1               5                   10                  15

Gln His Gly Ala Ala Ala Tyr Cys Asn Ser Glu Thr Ala Ser Gly Gln
                20                  25                  30
```

```
Lys Ile Thr Cys Asn Asp Asn Gly Cys Lys Gly Ile Glu Ala Asn Asn
                35                  40                  45

Ala Ile Ile Val Ala Ser Phe Val Gly Thr Gly Ile Gly Gly
 50                  55                  60

Tyr Val Ser Thr Asp Asn Val Arg Lys Glu Ile Val Leu Ser Ile Arg
 65                  70                  75                  80

Gly Ser Ser Asn Ile Arg Asn Trp Leu Thr Asn Val Asp Phe Gly Gln
                 85                  90                  95

Ser Ser Cys Ser Tyr Val Arg Asp Cys Gly Val His Thr Gly Phe Arg
                100                 105                 110

Asn Ala Trp Asp Glu Ile Ala Gln Arg Ala Arg Asp Ala Val Ala Lys
            115                 120                 125

Ala Arg Ala Met Asn Pro Ser Tyr Lys Val Ile Ser Thr Gly His Ser
130                 135                 140

Leu Gly Gly Ala Val Ala Thr Leu Gly Ala Ala Asp Leu Arg Ser Lys
145                 150                 155                 160

Gly Thr Ala Val Asp Ile Phe Thr Phe Gly Ala Pro Arg Val Gly Asn
                165                 170                 175

Ala Glu Leu Ser Ala Phe Ile Thr Ala Gln Ala Gly Gly Glu Phe Arg
            180                 185                 190

Val Thr His Gly Arg Asp Pro Val Pro Arg Leu Pro Pro Ile Val Phe
        195                 200                 205

Gly Tyr Arg His Thr Ser Pro Glu Tyr Trp Leu Ala Gly Gly Ala Ser
            210                 215                 220

Thr Lys Ile Asp Tyr Ser Val Asn Asp Ile Lys Val Cys Glu Gly Ala
225                 230                 235                 240

Ala Asn Leu Ala Cys Asn Gly Gly Thr Leu Gly Leu Asp Ile Ile Ala
                245                 250                 255

His Leu Arg Tyr Phe Gln Asn Thr Asp Ala Cys Thr Ala Gly Gly Ile
            260                 265                 270

Ser Trp Lys Arg Gly Asp Lys Ala Lys Arg Asp Glu Ile Pro Lys Arg
        275                 280                 285

Gln Glu Gly Met Thr Asp Glu Glu Leu Glu Gln Lys Leu Asn Asp Tyr
    290                 295                 300

Val Ala Met Asp Lys Glu Tyr Val Asp Ser His Lys Ile
305                 310                 315
```

<210> SEQ ID NO 12
<211> LENGTH: 952
<212> TYPE: DNA
<213> ORGANISM: Fusarium solani

<400> SEQUENCE: 12

```
gctattactg cctctcaatt ggattacgaa aacttcaagt tctacatcca acatggtgct      60
gcagcatatt gtaactcaga aactgcatct ggacagaaga tcacctgtaa cgataacgga     120
tgtaagggta tcgaagctaa taacgcaatt atagtggcca gtttcgttgg tacaggtacc     180
ggtatcggag ttatgtatc tactgacaat gttagaaaag agattgtctt gtccatccgt      240
ggatcctcta acattagaaa ctggttaacc aacgttgatt tcggtcaatc atcttgtagt     300
tacgtcaggg attgcggtgt tcatacagga tttaggaatg cttgggatga gattgcccaa     360
agagctcgtg atgcagttgc taaggccaga gctatgaacc caagttacaa ggtgatttct     420
actggtcatt cacttggggg agctgttgct actttgggtg ctgctgattt gcgttctaaa     480
ggcacagccg tcgacatttt cacttttggt gccccaagag tcggaaacgc tgaattgtcc     540
```

```
gcctttatta ccgctcaagc tggaggtgaa tttagggtta ctcacggacg agatcctgtt      600
ccaagactgc ctccaattgt ttttggttac agacatacgt ctcctgaata ctggttggct      660
ggaggtgctt ccaccaagat tgattactca gttaacgaca ttaaagtgtg tgaaggtgct      720
gctaaccttg cctgtaatgg aggtaccttg ggtttggaca ttattgctca tcttagatac      780
ttccagaaca ctgacgcttg cactgctggc ggtatttcct ggaagagagg tgataaggct      840
aagagagacg aaatcccaaa gcgtcaagaa ggcatgactg atgaagaact ggagcaaaag      900
ttgaatgatt atgtcgccat ggataaagag tacgttgact ctcacaagat cg             952
```